United States Patent [19]

Matsuo et al.

[11] Patent Number: 5,534,248
[45] Date of Patent: Jul. 9, 1996

[54] TOILETRY COMPOSITION FOR HAIR CARE

[75] Inventors: Takashi Matsuo, Chiba; Kumiko Adachi; Kazuyuki Yahagi, both of Tokyo, all of Japan

[73] Assignee: Kao Corporation, Tokyo, Japan

[21] Appl. No.: 127,066

[22] Filed: Sep. 27, 1993

[30] Foreign Application Priority Data

| Oct. 9, 1992 | [JP] | Japan | 4-271577 |
| Oct. 21, 1992 | [JP] | Japan | 4-282901 |
| Jun. 16, 1993 | [JP] | Japan | 5-144792 |
| Jun. 16, 1993 | [JP] | Japan | 5-144793 |

[51] Int. Cl.$^6$ ............... A61K 7/06; A61K 7/075
[52] U.S. Cl. ............... 424/70.28; 424/70.19; 424/70.31
[58] Field of Search ............... 424/70.28, 70.19, 424/70.31

[56] References Cited

U.S. PATENT DOCUMENTS

| 4,009,256 | 2/1977 | Nowak | 424/70.21 |
| 4,710,314 | 12/1987 | Madrange | 424/70.31 |
| 4,931,216 | 6/1990 | Igarashi | 424/70.21 |
| 5,057,311 | 10/1991 | Kamegai | 424/70.31 |
| 5,318,727 | 6/1994 | Ohtawa | 424/70.28 |

FOREIGN PATENT DOCUMENTS

| 0472107 | 2/1992 | European Pat. Off. . |
| 9210163 | 6/1992 | WIPO . |

*Primary Examiner*—Thurman K. Page
*Assistant Examiner*—Sally Gardner
*Attorney, Agent, or Firm*—Birch, Stewart, Kolasch & Birch

[57] ABSTRACT

A toiletry composition for hair care which is not irritative to the hair and skin and has an excellent conditioning effect and which comprises:

(a) a quaternary ammonium salt compound which contains aliphatic chains and, bonded to the aliphatic chain(s), a secondary or tertiary amino group and a quaternary ammonium group, and further which optionally contains an ether, an ester or an acyl group bonded within the aliphatic chain;

(b) an anionic surfactant; and (c) a water soluble polymer, and optionally (d) an alkylsaccharide surfactant.

7 Claims, No Drawings

TOILETRY COMPOSITION FOR HAIR CARE

BACKGROUND OF THE INVENTION

1. Field of the Invention

The present invention relates to a toiletry composition for hair care, that is, a hair care product, which is not irritative to the skin and hair and has an excellent conditioning effect.

Furthermore, the present invention relates to a toiletry composition for hair care, which is not irritative to the skin and hair and has excellent foamability, detergency and conditioning effect.

2. Description of the Related Art

In recent years, consumers' hair care behaviors including an increase in the frequency of shampooing and an increase in the number of people who maintain long hair, have largely changed. With these changes, the importance of preventing damage to the hair has become a priority and there has arisen a demand for a toiletry for hair care which is not irritative to the hair and is capable of improving the smoothness and capability of finger combing of the hair and one which is not irritative to the hair and has excellent foamability, detergency and conditioning effect.

To meet this demand, the present inventors have already proposed a cleaning composition which contains a specific quaternary ammonium salt compound and which has an excellent conditioning effect on the hair (refer to European Patent Publication-$A_2$ No. 0472107 published on Feb. 26, 1992).

Although the above-mentioned composition shows an excellent conditioning effect as a cleaning composition, it is poor in its conditioning effect as compared with common toiletries for hair care such as hair rinses and hair treatments. Thus, there is a demand for a toiletry for hair care, for example, a conditioning shampoo, having an improved conditioning effect, especially those which iS not irritative and has excellent foamability and detergency and a conditioning effect compare with that of a hair rinse.

DISCLOSURE OF THE INVENTION

SUMMARY OF THE INVENTION

Accordingly, the present inventors have conducted extensive studies in order to solve the above-mentioned problems. As a result, they have found that a toiletry composition for hair care containing a specific quaternary ammonium salt compound, an anionic surfactant and a water soluble polymer possesses low irritability to the skin and hair and exerts an excellent conditioning effect, thus completing the present invention.

Thus, the present invention provides a toiletry composition for hair care comprising:

(a) a quaternary ammonium salt compound which contains aliphatic chains and, bonded to the aliphatic chain(s), a secondary or tertiary amino group and a quaternary ammonium group, and further which optionally contains an ether, an ester or an acyl group bonded within the aliphatic chain;

(b) an anionic surfactant; and (c) a water soluble polymer.

In other word, the present invention relate to a toiletry for hair care characterized by containing:

(a) a quaternary ammonium salt type compound which comprises aliphatic chains or an ether, ester or acyl compound having aliphatic chains, a secondary or tertiary amino group and a quaternary ammonium group;

(b) an anionic surfactant; and (c) a water soluble polymer.

The water soluble polymer as component (c) is preferably a water soluble cationic polymer.

The quaternary ammonium salt compound is one comprising an aliphatic chain or an ether, ester or acyl compound having an aliphatic chain with a secondary or tertiary amino group and a quaternary ammonium group.

Preferable the quaternary ammonium salt compounds to be used as component (a) in the present invention are those represented by the following general formula (1):

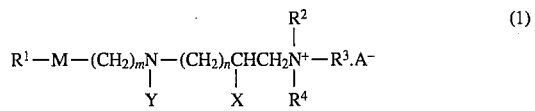

wherein $R^1$ represents a straight-chain or branched alkyl or alkenyl group having 7 to 35 carbon atoms;

$R^2$, $R^3$ and $R^4$ may be the same or different from one another and each represents an alkyl or hydroxyalkyl group having 1 to 4 carbon atoms or a hydrogen atom;

M represents a —CONG— (wherein G represents a hydrogen atom or an alkyl or hydroxyalkyl group having 1 to 3 carbon atoms), —O— or —COO— group;

X represents a hydrogen atom or a hydroxyl group;

$A^-$ represents a halogen ion or an organic anion;

m is a number of 2 or 3;

n is zero or an integer of 1 to 5, with the proviso that when n is 1, X is a hydrogen atom or a hydroxyl group, while when n is zero, 2, 3, 4 or 5, X is a hydrogen atom; and Y represents a hydrogen atom, a straight-chain or branched alkyl, alkenyl or hydroxyalkyl group having 1 to 36 carbon atoms or a group represented by the formula:

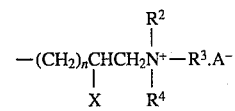

(wherein $R^2$, $R^3$, $R^4$, X, $A^-$ and n are each as defined above), with the proviso that when G is an alkyl or hydroxyalkyl group having 1 to 3 carbon atoms, Y is neither alkyl nor hydroxyalkyl group having 1 to 3 carbon atoms.

Among the quaternary ammonium salt compounds represented by the above general formula (1), those wherein $R^1$ represents a straight-chain or branched alkyl or alkenyl group having 7 to 21 carbon atoms, $R^2$, $R^3$ and $R^4$ may be the same or different from one another and each represents an alkyl or hydroxyalkyl group having 1 to 4 carbon atoms and Y represents a hydrogen atom, an alkyl or hydroxyalkyl group having 1 to 3 carbon atoms or a group represented by the formula:

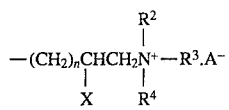

(wherein $R^2$, $R^3$, $R^4$, X, $A^-$ and n are each as defined above), with the proviso that when G is an alkyl or hydroxyalkyl group having 1 to 3 carbon atoms, Y is neither alkyl nor hydroxyalkyl group having 1 to 3 carbon atoms, are preferable.

Particularly Preferable quaternary ammonium salt compounds to be used as component (a) in the present invention are those represented by the following general formula (2):

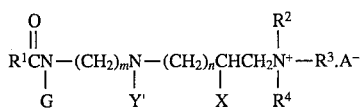

wherein $R^1$ represents a straight-chain or branched alkyl or alkenyl group having 7 to 35 carbon atoms; $R^2$, $R^3$ and $R^4$ may be the same or different from one another and each represents an alkyl or hydroxyalkyl group having 1 to 4 carbon atoms or a hydrogen atom;

G represents a hydrogen atom or an alkyl or hydroxyalkyl group having 1 to 3 carbon atoms;

X represents a hydrogen atom or a hydroxyl group;

$A^-$ represents a halogen ion or an organic anion;

m is a number of 2 or 3;

n is zero or an integer of 1 to 5, with the proviso that when n is 1, X is a hydrogen atom or a hydroxyl group, while when n is zero, 2, 3, 4 or 5, X is a hydrogen atom; and Y' represents a hydrogen atom, an alkyl or hydroxyalkyl group having 1 to 3 carbon atoms or a group represented by the formula:

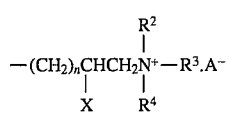

(wherein $R^2$, $R^3$, $R^4$, X, $A^-$ and n are each as defined above), with the proviso that when G is an alkyl or hydroxyalkyl group having 1 to 3 carbon atoms, Y' is neither alkyl nor hydroxyalkyl group having 1 to 3 carbon atoms.

Among the quaternary ammonium salt compounds represented by the above general formula (2), those wherein $R^1$ represents a straight-chain or branched alkyl or alkenyl group having 7 to 21 carbon atoms and, $R^2$, $R^3$ and $R^4$ may be the same or different from one another and each represents an alkyl or hydroxyalkyl group having 1 to 4 carbon atoms, are preferable.

Further, compounds represented by the general formula (3) are preferable as the quaternary ammonium salt compound of component (a), and these compounds may include compounds represented by the following general formulae (5) and (6) as by-products:

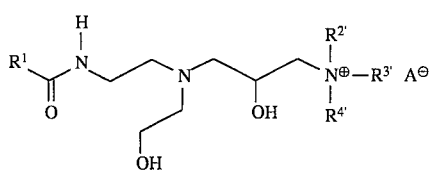

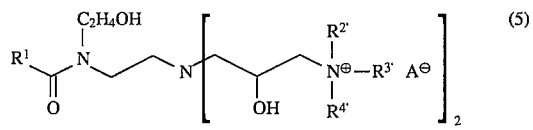

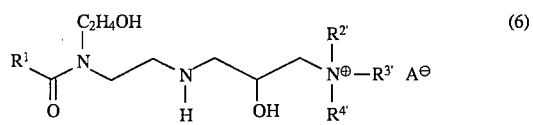

wherein $R^1$ represents a straight-chain or branched alkyl or alkenyl group having 7 to 35 carbon atoms; $R^{2'}$, $R^{3'}$ and $R^{4'}$ may be the same or different from one another and each represents an alkyl or hydroxyalkyl group having 1 to 4 carbon atoms; and $A^\ominus$ represents a halogen ion or an organic anion.

Among the quaternary ammonium salt compounds represented by the above general formula (3), those wherein $R^1$ represents a straight-chain or branched alkyl or alkenyl group having 7 to 21, in particular 11 to 17, carbon atoms are preferable. Those wherein the group represented by R'CO— is a lauroyl or myristoyl group and $R^{2'}$, $R^{3'}$ and $R^{4'}$ are all methyl groups are still preferable.

In addition, compounds represented by the general formula (4) are preferable as the quaternary ammonium salt compound of component (a):

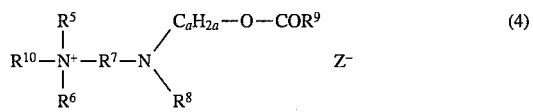

wherein $R^5$ and $R^6$ may be the same or different from each other and each represents an alkyl group having 1 to 4 carbon atoms;

$R^7$ represents an alkylene or alkenylene group having 2 to 6 carbon atoms;

$R^8$ represents a straight-chain or branched alkyl or alkenyl group having 4 to 36 carbon atoms;

$R^9$ represents a straight-chain or branched alkyl or alkenyl group having 7 to 35 carbon atoms;

$R^{10}$ represents a hydrogen atom or an alkyl or hydroxyalkyl group having 1 to 4 carbon atoms;

$Z^-$ represents a halogen ion, $½SO_4^{2-}$, $HSO_4^-$, $RCOO^-$ (wherein R represents an alkyl or alkenyl group having 1 to 4 carbon atoms in which a hydroxyl group may be substituted for a hydrogen atom) or an $R'SO_4^-$ (wherein R' represents an alkyl group having 1 to 4 carbon atoms), in other words, z represents a halogen atom, a sulfate, a bisulfate, a carboxylate having 1 to 4 carbon atoms which may be substituted with a hydroxyl group or an alkylsulfate having 1 to 4 carbon atoms; and a is an integer of 2 to 9.

Among the quaternary ammonium salt compounds represented by the above general formula (4), those wherein $R^5$ and $R^6$ are methyl groups, $R^7$ is an alkylene group having 2 or 3 carbon atoms, $R^8$ is a hardened beef tallow alkyl group or a hardened palm oil alkyl group, and $R^9CO$ is a hardened beef tallow fatty acid acyl group or a hardened palm oil fatty acid acyl group, are preferable.

Furthermore, the present inventors have found that a toiletry composition for hair care containing an alkylsaccharide surfactant, a specific quaternary ammonium salt compound, an anionic surfactant and a water soluble polymer is not irritative to the skin and hair, exhibits excellent performances in foaming and deterging and exerts an excellent conditioning effect, thus completing the present invention.

Thus, the present invention also provides a toiletry composition for hair care comprising the above-described components (a), (b) and (c), and (d) an alkylsaccharide surfactant.

The alkylsaccharide surfactant as component (d) is preferably a compound represented by the following general formula (I):

$$R-(OCH_2CH_2)_v-(J)_w \qquad (I)$$

wherein

R represents a straight-chain or branched, alkyl or alkenyl group having 8 to 18 carbon atoms or an alkyl- or alkenylphenyl group in which the alkyl or alkenyl group is a straight-chain or branched one and has 8 to 18 carbon atoms;

J represents a reducing sugar residue having 5 or 6 carbon atoms;

v is an average addition molar number of ethylene oxide number and is from 0 to 20; and w is an average number of the reducing sugar residues and is from 1 to 10.

Further scope and the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The quaternary ammonium salt compound (a) according to the present invention includes various compounds as described above. Among them, the quaternary ammonium salt compound represented by the above general formula (3) is produced by, for example, the following method.

As the following production flow sheet 1 shows, a fatty acid ($R^1CO_2H$) is reacted with aminoethylethanolamine represented by the following general formula (7) to form an imidazoline derivative represented by the following general formula (8). Next, this derivative is treated with an alkali and quaternized by reacting with a compound represented by the general formula (9). Thus a quaternary ammonium salt compound represented by the general formula (3) is synthesized. It is preferable from the viewpoints of the solubility of the water soluble polymer (c) in the toiletry composition for hair care according to the present invention and the viscosity properties of the toiletry composition according to the present invention to desalt the compound represented by the general formula (3) thus obtained by, for example, electrodialysis.

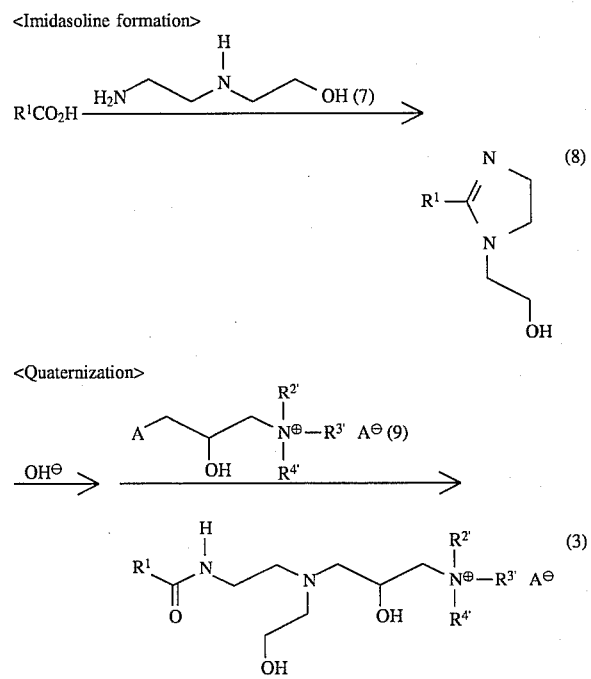

wherein $R^1$, $R^{2'}$, $R^{3'}$, $R^{4'}$ and $A^v$ are each as defined above.

The quaternary ammonium salt compound represented by the above general formula (4) to be used in the present invention is produced by, for example, the following method.

As the following production flow sheet 2 shows, an ester amine represented by the general formula (10) is reacted with an acidic substance represented by the general formula (11) or a quaternizing agent. Thus the target compound represented by the general formula (4) can be obtained.

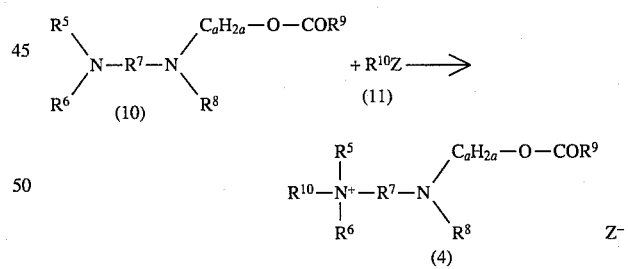

wherein $R^5$, $R^6$, $R^7$, $R^8$, $R^9$, $R^{10}$, Z and a are each as defined above.

Either one of such quaternary ammonium compounds or a combination of two or more thereof can be used as component (a). The content thereof in the toiletry composition for hair care according to the present invention preferably ranges from 0.1 to 20% by weight, still preferably from 1 to 10% by weight, based on the weight of the toiletry composition.

When the toiletry composition according to the present invention contains component (d), that is, an alkylsaccharide surfactant, the content of component (a) in the toiletry composition preferably ranges from 1 to 20% by weight still preferably from 2 to 10% by weight, based on the weight of the toiletry composition.

The anionic surfactant to be used as component (b) in the present invention includes the following compounds (i) to (xii).

(i) Straight-chain or branched alkylbenzenesulfonates having an alkyl group of 10 to 16 carbon atoms on the average.

(ii) Alkyl or alkenyl ether sulfates having a straight-chain or branched alkyl or alkenyl group of 10 to 20 carbon atoms on the average and containing 0.5 to 8 moles, on the average, per molecule of ethylene oxide, propylene oxide, butylene oxide, a mixture of ethylene oxide with propylene oxide at a ratio of 0.1/9.9 to 9.9/0.1 or a mixture of ethylene oxide with butylene oxide at a ratio of 0.1/9.9 to 9.9/0.1 added thereto.

(iii) Alkyl- or alkenylsulfates having an alkyl or alkenyl group of 10 to 20 carbon atoms on the average.

(iv) Olefinsulfonates having 10 to 20 carbon atoms, on the average, per molecule.

(v) Alkanesulfonates having 10 to 20 carbon atoms, on the average, per molecule.

(vi) Salts of saturated or unsaturated fatty acids having 10 to 24 carbon atoms, on the average, per molecule.

(vii) Alkyl or alkenyl ether carboxylates having an alkyl or alkenyl group of 10 to 20 carbon atoms on the average and containing 0.5 to 8 moles, on the average, per molecule of ethylene oxide, propylene oxide, butylene oxide, a mixture of ethylene oxide with propylene oxide at a ratio of 0.1/9.9 to 9.9/0.1 or a mixture of ethylene oxide with butylene oxide at a ratio of 0.1/9.9 to 9.9/0.1 added thereto.

(viii) Salts and/or esters of $\alpha$-sulfo fatty acids having an alkyl or alkenyl group having 10 to 20 carbon atoms on the average.

(ix) N-Acyl amino acid surfactants having an acyl group of 8 to 24 carbon atoms and a free carboxylate residue.

(x) Phosphoric mono- or diester surfactants having an alkyl or alkenyl group of 8 to 24 carbon atoms.

(xi) Sulfosuccinic esters of higher alcohols having 8 to 22 carbon atoms or ethoxylates thereof, or sulfo-succinic esters derived from higher fatty acid amides.

(xii) Ether sulfonates derived from higher fatty acid amides.

Examples of the counter ions of the anionic residues in these anionic surfactants include an alkali metal ion such as a sodium ion and a potassium ion; an alkaline earth metal ion such as a calcium ion and a magnesium ion; an ammonium ion; and an alkanolamine having 1 to 3 alkanol groups having 2 or 3 carbon atoms, for example, monoethanolamine, diethanolamine, triethanolamine and triisopropanolamine.

Among these anionic surfactants, (ii) alkyl ether sulfates, (iii) alkylsulfates, (vi) salts of saturated or unsaturated fatty acids, (ix) acylated amino acids, (x) phosphoric monoester surfactants and (xi) sulfosuccinic esters are particularly preferable. Suitable examples thereof include sodium polyoxyethylene lauryl ether sulfate (2 to 3 moles, on average, of ethylene oxide added), triethanolamine lauryl sulfate, sodium salts of coconut oil fatty acids, amide ether sulfates of coconut oil fatty acids, lauroyl-N-methyltaurine, lauroyl-N-methyl-$\beta$-alanine, disodium N-myristoyl-L-glutamate, disodium poly(e.g., 3 to 7)oxyethylene lauryl sulfosuccinate, lauryl phosphate, N-lauroyl-N'-carboxymethyl-N'-(2-hydroxyethyl)ethylenediamine/triethanolamine salt, sodium salt of N-lauroyl-N-(2-hydroxyethyl)-N',N'-bis(carboxymethyl)ethylenediamine and lauroyl-$\beta$-alanine.

Either one of such anionic surfactants or a combination of two or more thereof may be used as component (b). The content thereof in the toiletry composition for hair care according to the present invention preferably ranges from 1 to 20% by weight, still preferably from 2 to 15% by weight, particularly preferably from 5 to 15% by weight, based on the weight of the toiletry composition.

When the toiletry composition according to the present invention contains component (d), the content of component (b) in the toiletry composition preferably ranges from 1 to 20% by weight, still preferably from 3 to 15% by weight based on the weight of the toiletry composition.

The water soluble polymer to be used as component (c) in the present invention may be any of a natural polymer, a semisynthetic and a synthetic polymer and any of a cationic polymer, an anionic polymer, a nonionic polymer and so on.

Examples of the natural water soluble polymers include vegetable polymers such as gum arabic, gum tragacanth, galactan, guar gum, carob gum, gum karaya, carrageenan, pectin, agar, quince seed (*Cydonia oblonga*) and glycyrrhetinic acid, microbial polymers such as xanthan gum, dextran, succinoglucan and pullulan and protein hydrolysate polymers such as keratin decomposition derivatives.

Examples of the semisynthetic water soluble polymers include starch polymers such as cationic starch, carboxymethylstarch and methylhydroxypropylstarch, cellulose polymers such as a cationized cellulose derivative, methylcellulose, nitrocellulose, ethylcellulose, methylhydroxypropylcellulose, hydroxyethylcellulose, sodium cellulose sulfate, hydroxypropylcellulose, sodium carboxymethylcellulose (CMC), crystalline cellulose and cellulose powder, alginic acid polymers such as sodium alginate and alginic acid/propylene glycol ester and a cationized guar gum derivatives.

Examples of the synthetic water soluble polymers include a homopolymer of a diallyl quaternary ammonium salt; a diallyl quaternary ammonium salt/acrylamide copolymer; a quaternized polyvinylpyrrolidone derivative; a polyvinylpyrrolidone; a copolymer of vinylpyrrolidone with, for example, vinyl acetate or an alkylaminoacrylate; a lower alkyl half ester of a methyl vinyl ether/maleic anhydride copolymer; a copolymer of vinyl acetate with, for example, crotonic acid; a copolymer of acrylic acid and/or methacrylic acid with an alkyl acrylate and/or an alkyl methacrylate; a copolymer of acrylic acid with an alkyl acrylate and an N-alkylacrylamide; an amphoteric derivative of a copolymer of, for example, a dialkylaminoethyl methacrylate, a dialkylaminoethyl acrylate or diacetoneacrylamide with, for example, acrylic acid, methacrylic acid, an alkyl acrylate or an alkyl methacrylate; a terpolymer of hydroxypropyl acrylate with butylaminoethyl methacrylate and acrylic acid octylamide; and a copolymer of an alkylacrylamide, an acrylate, an alkylaminoalkylacrylamide and a polyethylene glycol methacrylate.

Among these water soluble polymers, water soluble cationic polymers containing an amino or ammonium group binded to the polymer chain or at least a dimethyldiallylammonium halide as a structural unit are particularly preferable. Examples of such water soluble cationic polymers include a cationized cellulose derivative, cationic starch, a cationized guar gum derivative, a homopolymer of a diallyl quaternary ammonium salt, a diallyl quaternary ammonium salt/acrylamide copolymer and a quaternized polyvinylpyrrolidone derivative.

Preferable examples of the cationized cellulose derivative are those represented by the following general formula (12):

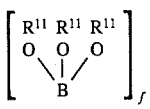 (12)

In the formula (12), B represents an anhydroglucose unit residue; f is an average degree of polymerization and is from 50 to 20,000; and each $R^{11}$ represents, independently of one another, a substituent represented by the following general formula (13):

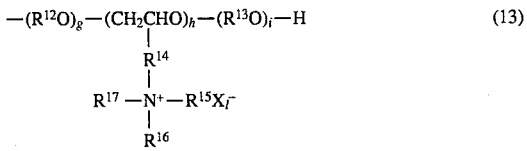 (13)

In the formula (13), each of $R^{12}$ and $R^{13}$ represents, independently of each other, an alkylene group having 2 or 3 carbon atoms; g is an integer of 0 to 10; h is an integer of 0 to 3; i is an integer of 0 to 10; $R^{14}$ represents an alkylene or hydroxyalkylene group having 1 to 3 carbon atoms; $R^{15}$, $R^{16}$ and $R^{17}$ may be the same or different from one another and each represents an alkyl, aryl or aralkyl group having up to 10 carbon atoms, or $R^{15}$ $R^{16}$ and $R^{17}$ may form a heterocyclic ring together with the nitrogen atom in the formula; and $X_1^{\ominus}$ represents an anion (for example, a chlorine ion, a bromine ion, an iodide ion, $\frac{1}{2}SO_4^{2-}$, $SO_3H^-$, $CH_3SO_4^-$, $1/3PO_4^{3-}$ or $NO_3^-$).

The degree of cation substitution on the cationized cellulose derivative, that is, the average value of h per anhydroglucose unit, to be used in the present invention ranges preferably from 0.01 to 1, still preferably from 0.02 to 0.5. The sum of g and i ranges from 1 to 3 on the average. A degree of cation substitution less than 0.01 is insufficient. Although the degree of cation substitution may exceed 1, it is preferable from the viewpoint of the reaction yield that it does not exceed 1. The average molecular weight of the cationized cellulose derivative to be used here preferably falls within a range of about 100,000 to 3,000,000.

Preferable cationic starches are those represented by the following general formula (14):

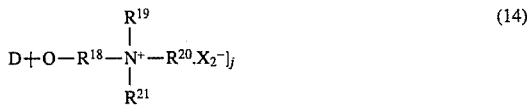 (14)

In the formula (14), D represents a starch residue; $R^{18}$ represents an alkylene or hydroxyalkylene group; $R^{19}$, $R^{20}$ and $R^{21}$ may be the same or different from one another and each represents an alkyl, aryl or aralkyl group having 10 or less carbon atoms, or two of $R^{19}$, $R^{20}$ and $R^{21}$ may form a heterocyclic ring together with the nitrogen atom in the formula; $X_2^-$ represents an anion (for example, a chlorine ion, a bromine ion, an iodide ion, $\frac{1}{2}SO_4^{2-}$, $SO_3H^-$, $CH_3SO_4^-$, $1/3PO_4^{3-}$ or $NO_3^-$); and j is a positive integer. The heterocyclic ring include, for example, a pyrrole ring and an imidazoline ring.

The degree of cation substitution on the cationic starch, that is, the average number of the cation group introduced thereinto per anhydrous glucose unit, to be used in the present invention ranges preferably from 0.01 to 1, still preferably 0.02 to 0.5. A degree of cation substitution less than 0.01 is insufficient. Although the degree of cation substitution may exceed 1, it is preferable from the viewpoint of the reaction yield that it does not exceed 1.

Preferable cationized guar gum derivatives are those represented by the following general formula (15):

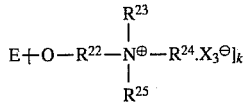 (15)

In the formula (15), E represents a guar gum residue; $R^{22}$ represents an alkylene or hydroxyalkylene group; $R^{23}$, $R^{24}$ and $R^{25}$ may be the same or different from one another and each represents an alkyl, aryl or aralkyl group having 10 or less carbon atoms, or two of $R^{23}$, $R^{24}$ and $R^{25}$ may form a heterocyclic ring together with the nitrogen atom in the formula; $X_3^{\ominus}$ represents an anion (for example, a chlorine ion, a bromine ion, an iodide ion, $\frac{1}{2}SO_4^{2-}$, $SO_3H^-$, $CH_3SO_4^-$, $1/3PO_4^{3-}$ or $NO_3^-$); and k is a positive integer. The heterocyclic ring include, for example, a pyrrole ring and an imidazoline ring.

The degree of cation substitution on the cationized guar gum derivative, that is, the average number of the cationic group introduced thereinto per sugar unit, to be used in the present invention ranges preferably from 0.01 to 1, still preferably 0.02 to 0.5. Cation polymers of this type are described in, for example, European Patent Publication-A Nos. 18717 (published on Nov. 12, 1980), 74264 (published on Mar. 16, 1983) and 93601 (published on Nov. 9th, 1983) and available from Celanese Stein Hall under tradename Jaguar.

Preferable cationic diallyl quaternary ammonium salt homopolymers and cationic diallyl quaternary ammonium salt/acrylamide copolymers are those represented by the following general formulae (16) or (17):

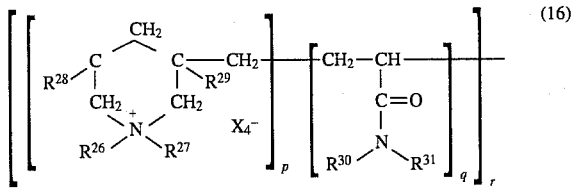 (16)

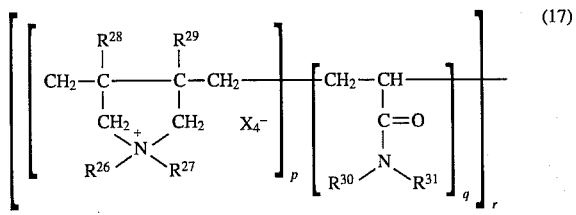 (17)

In the above formulae (16) and (17), $R^{26}$ and $R^{27}$ may be the same or different from each other and each represents a hydrogen atom, an alkyl group having 1 to 18 carbon atoms, a phenyl group, an aryl group, a hydroxyalkyl group, an amidoalkyl group, a cyanoalkyl group, an alkoxyalkyl group or a carboalkoxyalkyl group; $R^{28}$, $R^{29}$, $R^{30}$ and R may be the same or different from one another and each represents a hydrogen atom, a lower alkyl group having 1 to 3 carbon atoms or a phenyl group; $X_4^-$ represents an anion (for example, a chlorine ion, a bromine ion, an iodide ion, $\frac{1}{2}SO_4^{2-}$, $SO_3H^-$, $CH_3SO_4^-$, $1/3PO_4^{3-}$ or $NO_3^-$); p is an average degree of polymerization of the quaternary ammonium unit and is from 1 to 50; q is an average degree of polymerization of the amine unit and is from 0 to 50; and r is an average degree of polymerization and is from 150 to 8,000.

The average molecular weight of the diallyl quaternary ammonium salt homopolymer or the diallyl quaternary ammonium salt/acrylamide copolymer to be used in the present invention preferably falls within a range of from about 30,000 to 2,000,000, still preferably from 100,000 to 1,000,000.

Preferable quaternized polyvinylpyrrolidone derivatives are those represented by the following formula (18):

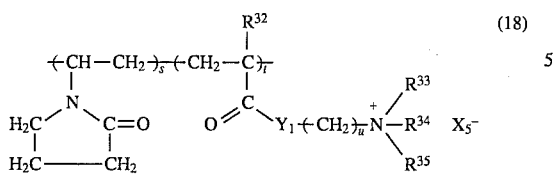

In the formula (18), $R^{32}$ represents a hydrogen atom or an alkyl group having 1 to 3 carbon atoms; $R^{33}$, $R^{34}$ and $R^{35}$ may be the same or different from one another and each represents a hydrogen atom, an alkyl group having 1 to 4 carbon atoms, a hydroxyalkyl group, an amidoalkyl group, a cyanoalkyl group, an alkoxyalkyl group or a carboalkoxyalkyl group; $Y_1$ represents an oxygen atom or an NH group in an amide bond; $X_5^-$ represents an anion [for example, a chlorine ion, a bromine ion, an iodide ion, $\frac{1}{2}SO_4^{2-}$, $SO_3H^-$, $R'SO_4^-$ (wherein R' represents an alkyl group having 1 to 4 carbon atoms), $\frac{1}{3}PO_4^{3-}$ or $NO_3^-$]; u is an integer of 1 to 10; and s plus t is from 20 to 8,000 on the average.

The average molecular weight of the quaternized polyvinylpyrrolidone derivative to be used in the present invention preferably falls within a range of from 10,000 to 2,000,000, still preferably from 50,000 to 1,500,000.

Either one of these water soluble polymers or a combination of two or more thereof may be used as component (c). These water soluble polymers are contained in the toiletry composition for hair care according to the present invention preferably in an amount of 0.01 to 2% by weight, still preferably 0.1 to 0.8% by weight, based on the weight of the toiletry composition.

When the toiletry composition according to the present invention contains component (d), the content of component (c) in the toiletry composition ranges preferably from 0.01 to 3% by weight, still preferably from 0.3 to 1.5% by weight based on the weight of the toiletry composition.

The toiletry composition for hair care according to the present invention may contain (d) an alkylsaccharide surfactant.

Examples of the alkylsaccharide surfactant as component (d) in the present invention include compounds represented by the general formula (I):

$$R\text{---}(OCH_2CH_2)_v\text{---}(J)_w \qquad (I)$$

wherein

R represents a straight-chain or branched, alkyl or alkenyl group having 8 to 18 carbon atoms or an alkyl- or alkenylphenyl group in which the alkyl or alkenyl group is a straight-chain or branched one and has 8 to 18 carbon atoms;

J represents a reducing sugar residue having 5 or 6 carbon atoms;

v is an average addition molar number of ethylene oxide number and is from 0 to 20; and w is an average number of the reducing sugar residues and is from 1 to 10.

In the general formula (I) described above, R represents a straight-chain or branched alkyl group having 8 to 18 carbon atoms, a straight-chain or branched alkenyl group having 8 to 18 carbon atoms or an alkyl- or alkenylphenyl group in which the alkyl or alkenyl group is a straight-chain or branched one and has 8 to 18 carbon atoms, preferably a straight-chain or branched alkyl group having 9 to 14 carbon atoms (such as nonyl group, decyl group, lauryl group and myristyl group). The saccharide part which is a hydrophilic group (J in the formula (I)) comprises a reducing sugar having 5 or 6 carbon atoms as a base unit. Preferably examples of the reducing sugar include glucose, galactose and fructose. The degree of polymerization of saccharide, S, i.e., w in the formula (I), ranges from 1 to 10 on the average.

An alkylsaccharide surfactant, which is represented by the above general formula (I) and which contains compounds represented by the following general formula (II), i.e., compounds having degree of polymerization, S, of 1 to 4, in an amount of 80% or more, is preferable.

$$R\text{---}(OCH_2CH_2)_x\text{---}(J)_y \qquad (II)$$

wherein

R represents a straight-chain or branched, alkyl or alkenyl group having 8 to 18 carbon atoms or an alkyl- or alkenylphenyl group in which the alkyl or alkenyl group is a straight-chain or branched one and has 8 to 18 carbon atoms;

J represents a reducing sugar residue having 5 or 6 carbon atoms;

x is 0 or a positive integer; and y is an integer of 1 to 4.

Further, taking account of the effect given by both the degree of polymerization, S, and the carbon atom number of the group R to the performances of the alkylsaccharide surfactant represented by the general formula (I), those wherein R has 8 to 11 carbon atoms and the degree of polymerization. S, ranges from 1 to 1.4 and those wherein R has 12 to 14 carbon atoms and the degree of polymerization, S, ranges from 1.5 to 4.0, are preferable. Furthermore, since the foaming power of the alkylsaccharide surfactant tends to get low when the degree of polymerization, S, is high, those represented by the general formula (I) wherein R has 8 to 11 carbon atoms and the degree of polymerization, S, ranges from 1 to 1.4 are especially preferable from the point of their foaming power. The average degree of polymerization of sugar, w, can be determined according to the proton NMR method.

Examples of the alkylsaccharide surfactant described above include β-alkylsaccharides such as octylglucoside, nonylglucoside, decylglucoside, decylmaltoside, polyoxyethylene(2E.O.) dodecylmaltoside, dodecylmaltoside and tridecylmaltoside, which are prepared according to the known method, e.g., the Koening-Knorr method, and those prepared from a reducing sugar such as glucose, galactose and maltose and a higher alcohol or polyoxyethylene alkyletheralcohol (see U.S. Pat. Nos. 3,839,318 and 3,598,865).

It is preferable that the toiletry composition for hair care according to the present invention contains 1 to 60% by weight, especially 2 to 30% by weight, based on the weight of the toiletry composition, of an alkylsaccharide surfactant(s) as component (a).

In addition to the quaternary ammonium salt compound as component (a), the anionic surfactant as component (b), the water soluble polymer as component (c) and optionally the alkylsaccharide surfactant as component (d) described above, the toiletry composition for hair care of the present invention may further, optionally contain, if necessary, various components commonly employed in toiletries, cosmetics, medicines or foods, for example, pharmaceutically efficacious components including anti-dandruff agents such as zinc pyrithione (Zpt), bactericides and vitamins; preservatives such as p-benzoic acid; humectants such as propylene glycol, glycerol, diethylene glycol monoethyl ether, sorbitol, panthenol and glycine betaine; coloring matters such as dyes and pigments; conditioning agents such as perfluoropolyether; pearling agents such as glycol ester; chitosan derivatives such as hydroxypropylchitosan; various fragrance mixtures; and those described in ENCYCLOPEDIA OF CONDITIONING RINSE INGREDIENTS (MICELLE PRESS, 1987), so long as the effects of the present invention are not deteriorated thereby.

The toiletry composition for hair care according to the present invention is excellent in the moistness during application and rinsing, gives a natural hair setting, enables smooth combing and is mild and lowly irritative to the skin and hair. Thus it is highly useful as a hair shampoo or a hair rinse.

Among the toiletry compositions according to the present invention, those containing component (d) is particularly useful as a hair shampoo because the composition gives creamy foam, exhibits excellent foaming, enables smooth finger combing during washing and rinsing, gives a natural hair setting, enables smooth combing and is mild and lowly irritative to the skin and hair.

EXAMPLES

The present invention will now be described in more detail with reference to tile following Examples which should not be considered to limit the scope of the present invention.

Example 1

Various toiletries for hair care having the compositions as specified in Table 1 were prepared to evaluate the performances on the basis of the following criteria. Table 1 shows the results.

<Criteria for evaluation>
Feeling of hair during application:
  ⊚: soft, smooth and highly capable of finger combing.
  ○: smooth and capable of finger combing.
  Δ: not smooth and resistant to finger combing.
  x: squeaky and tangled.
Capability of finger combing in rinsing:
  ⊚: completely free from squeaking and highly capable of finger combing.
  ○: slightly squeaky and capable of finger combing.
  Δ: somewhat squeaky and difficultly capable of finger combing.
  x: highly squeaky and poorly capable of finger combing.
Stickiness of hair after towel-drying and drying:
  ○: not sticky but oil-free.
  Δ: somewhat sticky.
  x: sticky.
Softness of hair after towel-drying:
  ⊚: very soft and flexible.
  ○: soft.
  Δ: somewhat poor in softness.
  x: stiff.
Hair setting after drying:
  ⊚: very smooth setting.
  ○: natural setting.
  Δ: somewhat poor setting.
  x: poor setting with hopping hairs.
Capability of combing after drying:
  ○: highly capable of combing.
  Δ: somewhat resistant to combing.
  x: poorly capable of combing at hair tips with tangling.
Skin irritation:
  ○: none or scarcely irritative.
  Δ: slightly irritative.
  x: moderately or seriously irritative.

TABLE 1

| | | Comparative product | | Invention product | | |
|---|---|---|---|---|---|---|
| | | 1 | 2 | 1 | 2 | 3 |
| Composition (wt. %) | (myristoyl-N-hydroxyethyl)aminoethyl-2-hydroxypropyltrimethylammonium chloride*1 | | | 4 | 6 | 6 |
| | sodium polyoxyethylene (3) lauryl sulfate | 8 | | 6 | | |
| | disodium polyoxyethylene (3) lauryl sulfosuccinate | | 8 | | 4 | |
| | disodium N-myristoyl-L-glutamate | | | | | 4 |
| | cationic polymer 1*2 | 0.5 | | 0.5 | | |
| | cationic polymer 2*3 | | 0.5 | | 0.5 | 0.5 |
| | common salt | | 1.0 | | | |
| | purified water | the balance | the balance | the balance | the balance | the balance |
| Results of evaluation | feeling of hair during application | ○ | Δ | ⊚ | ⊚ | ⊚ |
| | capability of finger combing in rinsing | Δ | ○ | ⊚ | ⊚ | ⊚ |
| | stickiness of hair after towel-drying | ○ | Δ | ⊚ | ⊚ | ⊚ |
| | softness of hair after towel-drying | x | ○ | ⊚ | ⊚ | ⊚ |
| | stickiness of hair after drying | ○ | Δ | ⊚ | ⊚ | ⊚ |
| | hair setting after drying | x | ○ | ⊚ | ⊚ | ⊚ |
| | capability of combing after drying | x | Δ | ○ | ○ | ○ |
| | skin irritation | x | ○ | ○ | ○ | ○ |

Note:

TABLE 1-continued

|  | Comparative product | | Invention product | | |
|---|---|---|---|---|---|
|  | 1 | 2 | 1 | 2 | 3 |

$$*^1 C_{13}H_{27}-\underset{O}{\overset{H}{\underset{\|}{C}}}-N-CH_2CH_2-N(CH_2CH_2OH)-CH_2\underset{OH}{CH}CH_2-\overset{CH_3}{\underset{CH_3}{N^+}}-CH_3 \quad Cl^-$$

*²cationic polymer 1
mfd. by Union Carbide Corp., Polymer JR-400 (cationized cellulose).
*³cationic polymer 2
mfd. by Merck & Co., Inc., Merquat 100 (poly-N,N-dimethyl-3,5-methylenepiperidinium chloride).

Example 2

A hair rinse composition of the following composition was prepared. This hair rinse composition was excellent in smoothness and softness of hair during application and rinsing and gave good hair setting after drying.

| (myristoyl-N-hydroxyethyl)aminoethyl-2-hydroxypropyltrimethylammonium chloride | 6% by weight |
|---|---|
| disodium polyoxyethylene (3) laurylsulfosuccinate | 4 |
| poly-N,N-dimethyl-3,5-methylenepiperidinium chloride*¹ | 0.5 |
| cetyl alcohol | 0.3 |
| dimethylpolysiloxane*² | 0.3 |
| dimethylpolysiloxane*³ | 0.3 |
| sodium benzoate | 0.5 |
| fragrance | 0.4 |
| coloring matter | 0.0001 |
| purified water | the balance |

Note:
*¹: mfd. by Merck Co., & Inc., Merquat 100.
*²: $(CH_3)_3SiO[(CH_3)_2SiO]_nSi(CH_3)_3$ n = 9000.
*³: mfd. by Shin-Etsu Chemical Co., Ltd., Silicone KF-96.

Example 3

A hair rinse composition of the following composition was prepared. This hair rinse composition was excellent in smoothness and softness of hair during application and rinsing and gave good hair setting after drying.

| (myristoyl-N-hydroxyethyl)aminoethyl-2-hydroxypropyltrimethylammonium chloride | 5% by weight |
|---|---|
| disodium N-myristoyl-L-glutamate | 5 |
| stearyltrimethylammonium chloride | 0.5 |
| poly-N,N-dimethyl-3,5-methylenepiperidinium chloride*¹ | 0.3 |
| cationized cellulose*² | 0.3 |
| propylene glycol | 3 |
| polyether-modified silicone*³ | 0.5 |
| dimethylpolysiloxane*⁴ | 0.3 |
| dimethylpolysiloxane*⁵ | 0.3 |
| sodium benzoate | 0.5 |
| fragrance | 0.4 |
| coloring matter | 0.0001 |
| purified water | the balance |

Note:
*¹: mfd. by Merck Co., & Inc., Merquat 100.
*²: mfd. by Union Carbide Corp., Polymer JR-400.
*³: mfd. by Shin-Etsu Chemical Co., Ltd., Silicone KF-6005.
*⁴: $(CH_3)_3SiO[(CH_3)_2SiO]_nSi(CH_3)_3$ n = 9000.
*⁵: mfd. by Shin-Etsu Chemical Co., Ltd., Silicone KF-96.

Example 4

A hair rinse composition of the following composition was prepared. This hair rinse composition was excellent in smoothness and softness of hair during application and rinsing and gave good hair setting after drying.

| quaternary ammonium salt compound represented by the following formula (19) | 4.5% by weight |
|---|---|

$$C_{11}H_{23}COC_2H_4NHCH_2\underset{OH}{CH}CH_2-\overset{CH_3}{\underset{CH_3}{N^+}}-CH_3 \quad Cl^- \quad (19)$$

| disodium N-myristoyl-N-glutamate | 5.5 |
|---|---|
| cationic polymer*¹ | 0.5 |
| common salt | 1.0 |
| liquid paraffin | 0.2 |
| sodium benzoate | 0.3 |
| fragrance | minute amount |
| coloring matter | minute amount |
| purified water | the balance |

Note:
*¹mfd. by Merck Co., & Inc., Merquat 100.

Example 5

A hair rinse composition of the following composition was prepared. This hair rinse composition was excellent in smoothness and softness of hair during application and rinsing and gave good hair setting after drying.

| quaternary ammonium salt compound represented by the following formula (20) | 5.0% by weight |
|---|---|

$$C_{12}H_{25}OC_3H_6NHCH_2\underset{OH}{CH}CH_2-\overset{CH_3}{\underset{CH_3}{N^+}}-CH_3 \quad Cl^- \quad (20)$$

| disodium polyoxyethylene (3) lauryl sulfosuccinate | 5.5 |
|---|---|
| cationic polymer*¹ | 0.5 |
| common salt | 1.0 |
| cetyl alcohol | 0.3 |
| sodium benzoate | 0.3 |
| fragrance | minute amount |
| coloring matter | minute amount |
| purified water | the balance |

Note:
*¹mfd. by Merck Co., & Inc., Merquat 100.

Example 6

A hair rinse composition of the following composition was prepared. This hair rinse composition was excellent in smoothness and softness of hair during application and rinsing and gave good hair setting after drying.

| | |
|---|---|
| quaternary ammonium salt compound represented by the following formula (21) | 4.5% by weight |

$$H-\overset{\overset{CH_3}{|}}{\underset{\underset{CH_3}{|}}{N^+}}-CH_2CH_2CH_2-N\overset{C_2H_4OCOR}{\underset{R'}{\diagdown}} \quad Cl^- \quad (21)$$

(-COR: hardened beef tallow fatty acid acyl group)
(R': hardened beef tallow alkyl group)

| | |
|---|---|
| disodium N-myristoyl-L-glutamate | 5.5 |
| cationic polymer*[1] | 0.5 |
| common salt | 1.0 |
| liquid paraffin | 0.2 |
| sodium benzoate | 0.3 |
| fragrance | minute amount |
| coloring matter | minute amount |
| purified water | the balance |

Note:
*[1]mfd. by Merck Co., & Inc., Merquat 100.

Example 7

A hair rinse composition of the following composition was prepared. This hair rinse composition was excellent in smoothness and softness of hair during application and rinsing and gave good hair setting after drying.

| | |
|---|---|
| quaternary ammonium salt compound represented by the following formula (22) | 5.0% by weight |

$$CH_3-\overset{\overset{CH_3}{|}}{\underset{\underset{CH_3}{|}}{N^+}}-CH_2CH_2CH_2-N\overset{C_2H_4OCOR}{\underset{R'}{\diagdown}} \quad Cl^- \quad (22)$$

(-COR: hardened beef tallow fatty acid alkyl group)
(R': hardened beef tallow silky group)

| | |
|---|---|
| disodium polyoxyethylene (3) lauryl sulfosuccinate | 5.5 |
| cationic polymer*[1] | 0.5 |
| common salt | 1.0 |
| cetyl alcohol | 0.3 |
| sodium benzoate | 0.3 |
| fragrance | minute amount |
| coloring matter | minute amount |
| purified water | the balance |

Note:
*[1]mfd. by Merck Co., & Inc., Merquat 100.

Example 8

A hair rinse composition of the following composition was prepared. This hair rinse composition was excellent in smoothness and softness of hair during application and rinsing and gave good hair setting after drying.

| | |
|---|---|
| quaternary ammonium salt compound represented by the following formula (23) | 6% by weight |

$$C_{13}H_{27}\underset{O}{\overset{H}{\underset{\|}{-C-N}}}-CH_2CH_2-\underset{\underset{OH}{|}}{N}-CH_2CH_2CH_2-\overset{\overset{CH_3}{|}}{\underset{\underset{CH_3}{|}}{N^+}}-CH_3 \quad Cl^- \quad (23)$$

with -OH substituent

| | |
|---|---|
| disodium polyoxyethylene (3) lauryl sulfosuccinate | 3 |
| common salt | 1 |
| carboxymethylcellulose*[1] | 0.5 |
| polyether-modified silicone*[2] | 0.5 |
| sodium benzoate | 0.3 |
| fragrance | minute amount |
| coloring matter | minute amount |
| purified water | the balance |

Note:
*[1]mfd. by Daicel Chemical Industries, Ltd. (product No. 1310).
*[2]mfd. by Shin-Etsu Chemical Co., Ltd., Silicone KF-6005.

Example 9

Various shampoos of Invention products 11 to 13 and Comparative products 3 to 9 having the compositions as specified in Table 2 were prepared to evaluate the performances on the basis of the following criteria and the criteria described in Example 1.

The performance in foaming was examined by the reverse stirring method. Feeling in touch of hair and the like was tested with five expert panelers as follows: 1 g of shampoo was applied on 20 g of hair (15 cm) of healthy Japanese women and was rinsed with water after foaming for one minute. Then, the hair was dried up by a dryer after towel-drying.

<Criteria for evaluation>

Foaming power:

⊚: exhibiting a very good foaming.

o: exhibiting a good foaming.

Δ: foaming but not sufficient.

x: little forming.

Feeling of hair during washing:

⊚: soft, smooth and highly capable of finger combing.

o: smooth and capable of finger combing.

Δ: not smooth and resistant to finger combing.

x: squeaky and tangled.

TABLE 2

| | | Invention product | | | Comparative product | | | | | | |
|---|---|---|---|---|---|---|---|---|---|---|---|
| | | 11 | 12 | 13 | 3 | 4 | 5 | 6 | 7 | 8 | 9 |
| Composition (wt. %) | alkylsaccharide surfactant*[1] | 10 | 10 | 10 | | | | 16 | 10 | 10 | |
| | (myristoyl-N-hydroxyethyl)aminoethyl-2- | 4 | 6 | 6 | 16 | | | | | | 6 |

TABLE 2-continued

| | | Invention product | | | Comparative product | | | | | | |
|---|---|---|---|---|---|---|---|---|---|---|---|
| | | 11 | 12 | 13 | 3 | 4 | 5 | 6 | 7 | 8 | 9 |
| | hydroxypropyltrimethylammonium chloride*2 | | | | | | | | | | |
| | sodium polyoxyethylene (3) lauryl sulfate | 6 | | | | 16 | | | | | |
| | disodium polyoxyethylene (3) lauryl sulfosuccinate | | 4 | | | | 16 | | 6 | | 4 |
| | disodium N-myristoyl-L-glutamate | | | 4 | | | | | | 6 | |
| | cationic polymer 1*3 | 0.5 | | | | 0.3 | 0.5 | | 0.3 | | |
| | cationic polymer 2*4 | | 0.5 | 0.3 | | | | 0.5 | | 0.5 | 0.5 |
| | purified water | the balance | the balance | the balance | the balance | the balance | the balance | the balance | the balance | the balance | the balance |
| Results of evaluation | forming power | ⊚ | ⊚ | ⊚ | o | ⊚ | Δ | ⊚ | ⊚ | ⊚ | x |
| | feeling of hair during washing | ⊚ | ⊚ | ⊚ | Δ | o | o | x | Δ | Δ | ⊚ |
| | capability of finger combing in rinsing | o | ⊚ | ⊚ | Δ | x | Δ | x | Δ | Δ | ⊚ |
| | softness of hair after towel-drying | o | ⊚ | ⊚ | Δ | x | Δ | x | Δ | Δ | ⊚ |
| | hair setting after drying | ⊚ | ⊚ | ⊚ | Δ | x | Δ | x | Δ | Δ | ⊚ |
| | capability of combing after drying | o | o | o | Δ | x | Δ | x | Δ | Δ | o |
| | skin irritation | o | o | o | o | x | o | o | o | o | o |

Note:
*1 alkylsaccharide surfactant represented by the general formula (I) with the priviso that R represents an alkyl group having 9 to 11 carbon atoms, J represents glucose, v is 0 and w is 1.3.

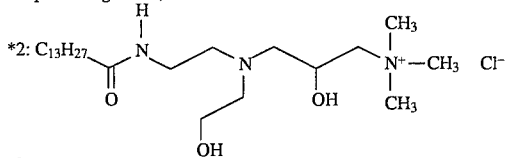

*3 cationic polymer 1
mfd. by Union Carbide Corp., Polymer JR-400 (cationized cellulose).
*4 cationic polymer 2
mfd. by Merck & Co., Inc., Merquat 100 (poly-N,N-dimethyl-3,5-methylenepiperidinium chloride).

Example 10

A shampoo of the following composition was prepared. When hair was washed with this shampoo, finger combing during washing and rinsing was smooth, hair was soft and naturally set after drying, and combing after drying was smooth.

| | |
|---|---|
| alkylsaccharide surfactant represented by the general formula (I) with the proviso that R represents an alkyl group having 9 to 11 carbon atoms, J represents glucose, v is 0 and w is 1.3. | 12% by weight |
| (myristoyl-N-hydroxyethyl)aminoethyl-2-hydroxypropyltrimethylammonium chloride | 5 |
| disodium N-myristoyl-L-glutamate | 5 |
| cationized cellulose*1 | 0.3 |
| poly-N,N-dimethyl-3,5-methylenepiperidinium chloride*2 | 0.3 |
| sodium benzoate | 0.5 |
| fragrance | appropriate amount |
| coloring matter | appropriate amount |
| pH modifier | appropriate amount |
| purified water | the balance |
| pH: 6.5 | |

Note:
*1: mfd. by Union Carbide Corp., Polymer JR-40
*2: mfd. by Merck Co., & Inc., Merquat 100.

Example 11

A shampoo of the following composition was prepared. When hair was washed with this shampoo, finger combing during washing and rinsing was smooth, hair was soft and naturally set after drying, and combing after drying was smooth.

| | |
|---|---|
| alkylsaccharide surfactant represented by the general formula (I) with the proviso that R represents an alkyl group having 9 to 11 carbon atoms. J represents glucose, v is 0 and w is 1.3. | 12% by weight |
| quaternary ammonium salt compound represented by the following formula (19) | 4.5 |

$$C_{11}H_{23}COC_2H_4NHCH_2CHCH_2-\underset{\underset{CH_3}{|}}{\overset{\overset{CH_3}{|}}{N^+}}-CH_3 \quad Cl^- \quad (19)$$
$$\hspace{4cm} OH$$

| | |
|---|---|
| disodium polyoxyethylene (3) lauryl sulfosuccinate | 5.5 |
| cationic polymer*1 | 0.5 |
| cetyl alcohol | 1.0 |
| common salt | 0.3 |
| sodium benzoate | 0.3 |
| fragrance | appropriate amount |
| coloring matter | appropriate amount |
| purified water | the balance |

Note:
*1 mfd. by Merck Co., & Inc., Merquat 100.

Example 12

A shampoo of the following composition was prepared. When hair was washed with this shampoo, finger combing during washing and rinsing was smooth, hair was soft and naturally set after drying, and combing after drying was smooth.

| | |
|---|---|
| alkylsaccharide surfactant represented by the general formula (I) with the proviso that R represents an alkyl group having 9 to 11 carbon atoms. J represents glucose, v is 0 and w is 1.3. | 13% by weight |
| quaternary ammonium salt compound represented by the following formula (20) | 4.5 |

$$C_{12}H_{25}OC_3H_6NHCH_2\underset{OH}{CH}CH_2-\underset{CH_3}{\overset{CH_3}{\underset{|}{\overset{|}{N^+}}}}-CH_3 \quad Cl^- \quad (20)$$

| | |
|---|---|
| sodium polyoxyethylene (3) lauryl sulfate | 5.5 |
| cationic polymer*¹ | 0.5 |
| liquid paraffin | 0.2 |
| common salt | 0.3 |
| sodium benzoate | 0.3 |
| fragrance | appropriate amount |
| coloring matter | appropriate amount |
| purified water | the balance |

Note:
*¹mfd. by Merck Co., & Inc., Merquat 100.

Example 13

A shampoo of the following composition was prepared. When hair was washed with this shampoo, finger combing during washing and rinsing was smooth, hair was soft and naturally set after drying, and combing after drying was smooth.

| | |
|---|---|
| alkylsaccharide surfactant represented by the general formula (I) with the proviso that R represents an alkyl group having 9 to 11 carbon atoms. J represents glucose, v is 0 and w is 1.3. | 12% by weight |
| quaternary ammonium salt compound represented by the following formula (21) | 4.5 |

$$H-\underset{CH_3}{\overset{CH_3}{\underset{|}{\overset{|}{N^+}}}}-CH_2CH_2CH_2-N\underset{R'}{\overset{C_2H_4OCOR}{\diagup\diagdown}} \quad Cl^- \quad (21)$$

(-COR: hardened beef tallow fatty acid acryl group)
(R': hardened beef tallow alkyl group)

| | |
|---|---|
| disodium polyoxyethylene (3) lauryl sulfosuccinate | 5.5 |
| cationic polymer*¹ | 0.5 |
| cetyl alcohol | 1.0 |
| common salt | 0.3 |
| sodium benzoate | 0.3 |
| fragrance | appropriate amount |
| coloring matter | appropriate amount |
| purified water | the balance |

Note:
*¹mfd. by Merck Co., & Inc., Merquat 100.

Example 14

A shampoo of the following composition was prepared. When hair was washed with this shampoo, finger combing during washing and rinsing was smooth, hair was soft and naturally set after drying, and combing after drying was smooth.

| | |
|---|---|
| alkylsaccharide surfactant represented by the general formula (I) with the proviso that R represents an alkyl group having 9 to 11 carbon atoms. J represents glucose, v is 0 and w is 1.3. | 13% by weight |
| quaternary ammonium salt compound represented by the following formula (22) | 4.5 |

$$CH_3-\underset{CH_3}{\overset{CH_3}{\underset{|}{\overset{|}{N^+}}}}-CH_2CH_2CH_2-N\underset{R'}{\overset{C_2H_4OCOR}{\diagup\diagdown}} \quad Cl^- \quad (22)$$

(-COR: hardened beef tallow fatty acid acryl group)
(R': hardened beef tallow alkyl group)

| | |
|---|---|
| sodium polyoxyethylene (3) lauryl sulfate | 5.5 |
| cationic polymer*¹ | 0.5 |
| liquid paraffin | 0.2 |
| common salt | 0.3 |
| sodium benzoate | 0.3 |
| fragrance | appropriate amount |
| coloring matter | appropriate amount |
| purified water | the balance |

Note:
*¹mfd. by Merck Co., & Inc., Merquat 100.

Example 15

A shampoo of the following composition was prepared. When hair was washed with this shampoo, finger combing during washing and rinsing was smooth, hair was soft and naturally set after drying, and combing after drying was smooth.

| | |
|---|---|
| alkylsaccharide surfactant represented by the general formula (I) with the proviso that R represents an alkyl group having 9 to 11 carbon atoms. J represents glucose, v is 0 and w is 1.3. | 12% by weight |
| quaternary ammonium salt compound represented by the following formula (23) | 6 |

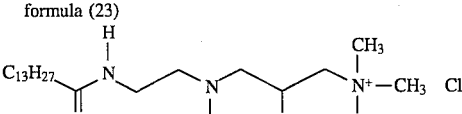

| | |
|---|---|
| disodium N-myristoyl-L-glutamate | 3 |
| carboxymethylcellulose*¹ | 0.5 |
| polyester-modified silicone*² | 0.5 |
| sodium benzoate | 0.3 |
| fragrance | appropriate amount |
| coloring matter | appropriate amount |
| purified water | the balance |

Note:
*¹mfd. by Daicel Chemical Industries, Ltd. (product No. 1310).
*²mfd. by Shin-Etsu Chemical Co., Ltd., Silicone KF-6005.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What we claim is:

1. A toiletry composition for hair care comprising:
   (a) a quaternary ammonium salt compound represented by the following general formula (4):

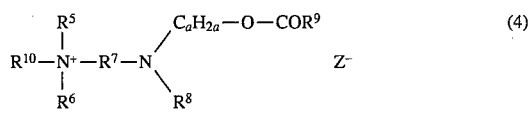

(4)

wherein
- $R^5$ and $R^6$ may be the same or different from each other and each represents an alkyl group having 1 to 4 carbon atoms;
- $R^7$ represents an alkylene or alkenylene group having 2 to 6 carbon atoms;
- $R^8$ represents a straight-chain or branched alkyl or alkenyl group having 4 to 36 carbon atoms;
- $R^9$ represents a straight-chain or branched alkyl or alkenyl group having 7 to 35 carbon atoms;
- $R^{10}$ represents a hydrogen atom or an alkyl or hydroxyalkyl group having 1 to 4 carbon atoms;
- $Z^-$ represents a halogen ion, $½SO_4^{2-}$, $HSO_4^-$, $RCOO^-$ wherein R represents an alkyl or alkenyl group having 1 to 4 carbon atoms in which a hydroxyl group may substitute for a hydrogen atom or an $R'SO_4^-$ (wherein R' represents an alkyl group having 1 to 4 carbon atoms; and
- a is an integer of 2 to 9;

(b) an anionic surfactant; and
(c) a water soluble polymer.

2. The toiletry composition for hair care as claimed in claim 1, wherein the compound represented by the general formula (4) is one wherein $R^5$ and $R^6$ are methyl groups, $R^7$ is an alkylene group having 2 or 3 carbon atoms, $R^8$ is a hardened beef tallow alkyl group or a hardened palm oil alkyl group, and $R^9CO$ is a hardened beef tallow fatty acid acyl group or a hardened palm oil fatty acid acyl group.

3. The toiletry composition for hair care as claimed in claim 1, wherein said water soluble polymer as component (c) is a water soluble cationic polymer.

4. The toiletry composition for hair care as claimed in claim 1, which comprises 0.1 to 20% by weight of component (a), 1 to 20% by weight of component (b) and 0.01 to 2% by weight of component (c), based on the weight of the toiletry composition.

5. The toiletry composition for hair care as claimed in claim 1, which further contains (d) an alkylsaccharide surfactant.

6. The toiletry composition for hair care as claimed in claim 5, wherein said alkylsaccharide surfactant as component (d) is represented by the following general formula (I):

wherein
- R represents a straight-chain or branched, alkyl or alkenyl group having 8 to 18 carbon atoms or an alkyl- or alkenylphenyl group in which the alkyl or alkenyl group is a straight-chain or branched one and has 8 to 18 carbon atoms;
- J represents a reducing sugar residue having 5 or 6 carbon atoms;
- v is an average addition molar number of ethylene oxide number and is from 0 to 20; and
- w is an average number of the reducing sugar residues and is from 1 to 10.

7. The toiletry composition for hair care as claimed in claim 5, which comprises 1 to 20% by weight of component (a), 1 to 20% by weight of component (b), 0.01 to 3% by weight of component (c) and 1 to 60% by weight of component (d), based on the weight of the toiletry composition.

* * * * *